United States Patent [19]
Borcherding et al.

[11] Patent Number: 5,605,903
[45] Date of Patent: Feb. 25, 1997

[54] CARBOCYCLIC NUCLEOSIDE ANALOGS USEFUL AS IMMUNOSUPPRESSANTS

[75] Inventors: David R. Borcherding, Overland Park; Carl K. Edwards, III, Olathe, both of Kans.; Ronald E. Esser, Kansas City, Mo.; Douglas L. Cole, Carlsbad, Calif.

[73] Assignee: Hoechst Marion Roussel, Inc., Cincinnati, Ohio

[21] Appl. No.: 408,365

[22] Filed: Mar. 22, 1995

Related U.S. Application Data

[62] Division of Ser. No. 336,706, Nov. 8, 1994, Pat. No. 5,470,857, which is a continuation of Ser. No. 212,338, Mar. 14, 1994, abandoned, which is a continuation of Ser. No. 123,577, Sep. 17, 1993, abandoned, which is a continuation of Ser. No. 824,413, Jan. 23, 1992, abandoned, which is a continuation-in-part of Ser. No. 748,173, Aug. 23, 1991, abandoned, which is a continuation-in-part of Ser. No. 582,265, Sep. 14, 1990, abandoned.

[51] Int. Cl.$^6$ .......................... A61K 31/435; A61K 31/52
[52] U.S. Cl. .......................... 514/258; 514/261; 514/299; 514/303
[58] Field of Search .................................. 514/258, 261, 514/299, 303

[56] References Cited

U.S. PATENT DOCUMENTS

| | | | |
|---|---|---|---|
| 3,917,837 | 11/1975 | Lin et al. | 544/276 |
| 4,742,064 | 5/1988 | Vince et al. | 514/258 |
| 4,845,215 | 7/1989 | Shimada et al. | 544/265 |
| 4,859,677 | 8/1989 | Borchardt et al. | 514/261 |
| 4,916,224 | 4/1990 | Vince et al. | 544/254 |
| 4,954,504 | 9/1990 | Chen et al. | 514/265 |
| 5,039,689 | 8/1991 | Daluge | 514/359 |
| 5,063,233 | 11/1991 | Chen et al. | 514/266 |
| 5,089,500 | 2/1992 | Daluge | 514/261 |
| 5,100,896 | 3/1992 | Borthwick et al. | 514/258 |
| 5,126,452 | 6/1992 | Vince et al. | 544/276 |
| 5,144,034 | 9/1992 | Johnson et al. | 544/276 |
| 5,187,174 | 2/1993 | Shuto et al. | 514/261 |
| 5,244,896 | 9/1993 | Borcherding et al. | 514/265 |

FOREIGN PATENT DOCUMENTS

| | | |
|---|---|---|
| 0267878 | 5/1988 | European Pat. Off. . |
| 0369409 | 5/1990 | European Pat. Off. . |
| 0475411 | 3/1992 | European Pat. Off. . |
| 91/15489 | 10/1991 | WIPO . |

OTHER PUBLICATIONS

Trost et al., Journal of the American Chemical Society, 1988, 110, 621–622.
Muftuoglu et al., Recent Advances in Immunology, 1984, Plenum Publishing, pp. 192–209.
Herbert et al., A Dictionary of Immunology, 1977, p. 112.
Rosen et al., Dictionary of Immunology, Rosen et al., 1989, pp. 9, 18, 69–70, 155, 188.
Huffer et al., Introduction to Human Immunology, 1986, pp. 148–161, and 169–176.
Coe et al., Journal of the Chemical Society, Chemical Communications, 1991, 312–314.
Jahne et al., Tetrahedron Letters, 33(37), 1992, 5335–5338.
Edwards et al., Science, 239:769–771, (Feb. 12, 1988).
Sinha et al., Science, 248:1380–1388, (Jun. 15, 1990).
Esser et al., Int. J. Tiss. Reac. XI(6)291–300, (1989).
R. E. Hanschumacher, Goodman and Gilman's, "The Pharmacological Basis of Therapeutics, 8th Ed., Pergamon Press," Sec. XIII Drugs Used for Immunosuppression, Chap. 53, Immunosuppressive Agents, pp. 1264–1276 1992.
USAN and the USP dictionary of drug names, Carolyn A. Feeger, Editor, pp. 31,66, and 408, compilation of USAN selected and released from (Jun. 15, 1961–Jun. 15, 1993).
PDR 43 Ed. 1989 Physicans' Desk Reference, Publisher E. R. Barnhart, pp. 773–774.
Trost, et al., J. Am. Chem. Soc. vol. 110(2), 621–622, (1988).
Hasobe, et al., FASEB Journal vol. 4, A1771 (Abstr. #455) (1990).
Ault–Riche, et al., FASEB Journal vol. 4, A2050 (Abstr. #2064) (1990).
Wolf, et al., 199th ACS National Meeting, Boston, Mass., Apr. 1990, Abstract #27.
Recent Advances in Immunology, Muftuoglu, et al., 1984, Plenum Press, pp. 191–209.
Introduction to Human Immunology, Huffer et al., 1986 Jones & Bartlett Publishers, Inc., pp. 148–161, 169–176.
A Dictionary of Immunology, Herbert et al., 1977, p. 112.
Dictionary of Immunology, Rosen et al., 1989, Elsevier Publishing Co., Inc. pp. 9, 18, 69–70, 155 & 188.
G. Jahne et al., Tetrahedron Letters, vol. 33, No. 37, pp. 5335–5338 (1992).
Recent Advances on Immunology, Müftüoglu et al. ed., 1984, Plenum Publishing pp. 191–209.
Introduction to Human Immunology, Mutter et al.. 1986, pp. 148–161, 169–176.
A Dictionary of Immunology, Herbert et al., 1977, p. 112.
Dictionary of Immunology, Rosen et al., 1989, pp. 9, 18, 69, 70, 155, 188.

*Primary Examiner*—Matthew V. Grumbling
*Attorney, Agent, or Firm*—T. Helen Payne

[57] ABSTRACT

This invention relates to a method of effecting immunosuppression in a patient in need thereof comprising administering an effective amount of a compound of the formula (1)

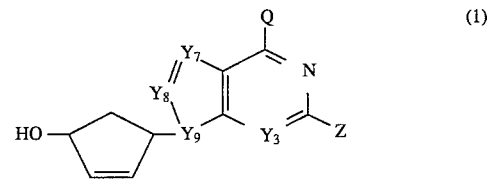

wherein
  the hydroxy substituent on the cyclopentenyl ring is in the CIS configuration relative to the bicyclic substituent,
  $Y_3$, $Y_7$, $Y_8$ and $Y_9$ are each independently nitrogen or a CH group,
  Q is $NH_2$, halogen or hydrogen, and
  Z is hydrogen, halogen, or $NH_2$;
or a pharmaceutically-acceptable salt thereof.

12 Claims, No Drawings

CARBOCYCLIC NUCLEOSIDE ANALOGS USEFUL AS IMMUNOSUPPRESSANTS

CROSS-REFERENCE TO RELATED APPLICATION

This is a division of application Ser. No. 08/336,706, filed Nov. 8, 1994, now U.S. Pat. No. 5,470,857 which is a continuation of application Ser. No. 08/212,338, filed Mar. 14, 1994, now abandoned, which is a continuation of application Ser. No. 08/123,557, filed Sep. 17, 1993, now abandoned, which is a continuation of application Ser. No. 07/824,413, filed Jan. 23, 1992, now abandoned, which is a continuation-in-part of application Ser. of 07/748,173, filed Aug. 23, 1991, now abandoned, which is a continuation-in-part of application Ser. No. 07/582,265, filed Sep. 14, 1990, now abandoned, which are herein incorporated by reference.

FIELD OF THE INVENTION

This invention relates to certain carbocyclic nucleoside analogs which are useful as immunosuppressants.

BACKGROUND OF THE INVENTION

Immunity is concerned with the recognition and disposal of foreign antigenic material which is present in the body. Typically the antigens are in the form of particulate matter (i.e., cells, bacteria, etc.) or large protein or polysaccharide molecules which are recognized by the immune system as being "non-self", i.e., detectably different or foreign from the animals own constituents. Potential antigens can be a variety of substances, often proteins, which are most frequently located on the outer surfaces of cells. For example, potential antigens can be found on pollen grains, tissue grafts, animal parasites, viruses, and bacteria. Once the antigenic material is recognized as "non-self" by the immune system, natural (non-specific) and/or adaptive immune responses can be initiated and maintained by the action of specific immune cells, antibodies and the complement system. Under certain conditions, including in certain disease states, an animal's immune system will recognize its own constituents as "non-self" and initiate an immune response against "self" material.

An immune response can be carried out by the immune system by means of natural or adaptive mechanisms, each of which are composed of both cell-mediated and humoral elements. Natural mechanisms for immune response refer to those mechanisms involved in essentially non-specific immune reactions which involve the complement system and myeloid cells alone, such as macrophages, mast cells and polymorphonuclear leukocytes (PMN), in reacting to certain bacteria, viruses, tissue damage and other antigens. These natural mechanisms provide what is referred to as natural immunity. Adaptive mechanisms for immune response refer to those mechanisms which are mediated by lymphocytes (T and B cells) and antibodies which can respond selectively to thousands of different materials recognized as "non-self". These adaptive mechanisms provide what is referred to as adaptive immunity and lead to a specific memory and a permanently altered pattern of response in adaptation to the animal's own environment. Adaptive immunity can be provided by the lymphocytes and antibodies alone or, more commonly, can be provided by the interaction of lymphocytes and antibodies with the complement system and myeloid cells of the natural mechanisms of immunity. The antibodies provide the humoral element of the adaptive immune response and the T-cells provide the cell-mediated element of the adaptive immune response.

Natural mechanisms of immune response involve phagocytosis by macrophages and PMN whereby foreign material or antigen is engulfed and disposed of by these cells. In addition, macrophages can kill some foreign cells through its cytotoxic effects. The complement system which is also involved in natural immunity is made up of various peptides and enzymes which can attach to foreign material or antigen and thereby promote phagocytosis by macrophages and PMN, or enable cell lysis or inflammatory effects to take place.

Adaptive mechanisms of immune response involve the actions against specific antigens of antibody secreted by B-lymphocytes (or B-cells) as well as the actions of various T-lymphocytes (or T-cells) on a specific antigen, on B-cells, on other T-cells and on macrophages.

Antibodies, which are responsible for the humoral aspect of adaptive immunity, are serum globulins secreted by B-cells with a wide range of specificity for different antigens. Antibodies are secreted in response to the recognition of specific antigens and provide a variety of protective responses. Antibodies can bind to and neutralize bacterial toxins and can bind to the surface of viruses, bacteria, or other cells recognized as "non-self" and thus promote phagocytosis by PMN and macrophages. In addition, antibodies can activate the complement system which further augments the immune response against the specific antigen.

Lymphocytes are small cells found in the blood which circulate from the blood, through the tissues, and back to the blood via the lymph system. There are two major subpopulations of lymphocytes called B-cells and T-cells. B-cells and T-cells are both derived from the same lymphoid stem cell with the B-cells differentiating in the bone marrow and the T-cells differentiating in the thymus. The lymphocytes possess certain restricted receptors which permit each cell to respond to a specific antigen. This provides the basis for the specificity of the adaptive immune response. In addition, lymphocytes have a relatively long lifespan and have the ability to proliferate clonally upon receiving the proper signal. This property provides the basis for the memory aspect of the adaptive immune response.

B-cells are the lymphocytes responsible for the humoral aspect of adaptive immunity. In response to recognition of a specific foreign antigen, a B-cell will secrete a specific antibody which binds to that specific antigen. The antibody neutralizes the antigen, in the case of toxins, or promotes phagocytosis, in the case of other antigens. Antibodies also are involved in the activation of the complement system which further escalates the immune response toward the invading antigen.

T-cells are the lymphocytes responsible for the cell-mediated aspect of adaptive immunity. There are three major types of T-cells, i.e., the Cytotoxic T-cells, Helper T-cells and the Suppressor T-cells. The Cytotoxic T-cells detects and destroys cells infected with a specific virus antigen. Helper T-cells have a variety of regulatory functions. Helper T-cells, upon identification of a specific antigen, can promote or enhance an antibody response to the antigen by the appropriate B-cell and it can promote or enhance phagocytosis of the antigen by macrophages. Suppressor T-cells have the effect of suppressing an immune response directed toward a particular antigen.

The cell-mediated immune response is controlled and monitored by the T-cells through a variety of regulatory messenger compounds secreted by the myeloid cells and the lymphocyte cells. Through the secretion of these regulatory messenger compounds, the T-cells can regulate the proliferation and activation of other immune cells such as B-cells, macrophages, PMN and other T-cells. For example, upon binding a foreign antigen, a macrophage or other antigen presenting cell can secrete interleukin-1 (IL-1) which activates the Helper T-cells. T-cells in turn secrete certain lymphokines, including interleukin-2 (IL-2) and γ-interferon, each of which have a variety of regulatory effects in the cell-mediated immune response. Lymphokines are a large family of molecules produced by T-cells (and sometimes B-cells) including IL-2, which promotes the clonal proliferation of T-cells;

MAF or macrophage activation factor, which increases many macrophage functions including phagocytosis, intracellular killing and secretion of various cytotoxic factors;

NAF or neutrophil activation factor, which increases many functions of the PMN including phagocytosis, oxygen radical production, bacterial killing, enhanced chemotaxis and enhanced cytokine production;

MIF or macrophage migration factor, which by restricting the movement of macrophages, concentrates them in the vicinity of the T-cell;

γ-interferon, which is produced by the activated T-cell and is capable of producing a wide range of effects on many cells including inhibition of virus replication, induction of expression of class II histocompatibility, molecules allowing these cells to become active in antigen binding and presentation, activation of macrophages, inhibition of cell growth, induction of differentiation of a number of myeloid cell lines.

Activated macrophages and PMNs, which provide an enhanced immune response as part of the cell-mediated adaptive immunity, are characterized as having increased production of reactive oxygen intermediates. This increased production of reactive oxygen intermediates, or respiratory burst, is known as "priming". Certain lymphokines, such as γ-interferon, trigger this respiratory burst of reactive oxygen intermediates in macrophages and PMNs. Thus, lymphokines, such as γ-interferon, which are secreted by the T-cells provide an activation of these macrophages and PMNs which results in an enhanced cell-mediated immune response.

The immune response can provide an immediate or a delayed type of response. Delayed-type hypersensitivity is an inflammatory reaction which occurs in immune reactive patients within 24–48 hours after challenge with antigen and is the result primarily of a cell-mediated immune response. In contrast, immediate-type hypersensitivity, such as that seen in anaphylactic or Arthus reactions, is an inflammatory reaction which occurs in immune reactive patients within minutes to a few hours after challenge with antigen and is the result primarily of humoral or antibody-mediated immune response.

The ability of the immune system, and in particular the cell-mediated immune system, to discriminate between "self" and "non-self" antigens is vital to the functioning of the immune system as a specific defense against invading microorganisms. "Non-self" antigens are those antigens on substances in the body which are detectably different or foreign from the animals own constituents and "self" antigens are those antigens which are not detectably different or foreign from the animals own constituents. Although the immune response is a major defense against foreign substances which can cause disease, it cannot distinguish between helpful and harmful foreign substances and destroys both.

There are certain situations, such as with an allogeneic transplant or in "graft versus host" disease, where it would be extremely useful to suppress the immune response in order to prevent the rejection of helpful foreign tissue or organs. Allogeneic tissues and organs are tissues and organs from a genetically different member of the same species. "Graft versus host" disease occurs where the transplanted tissue, for example in a bone marrow transplant, contains allogeneic T-cells of the donor which cause an immune response against the recipient's own tissues. Although both humoral and cell-mediated immune responses play a role in the rejection of allogeneic tissues and organs, the primary mechanism involved is the cell-mediated immune response. Suppression of the immune response, and in particular, suppression of cell-mediated immune response, would thus be useful in preventing such rejection of allograft tissues and organs. For example, cyclosporin A is currently used as an immunosuppressive agent in the treatment of patients receiving allogeneic transplants and in "graft versus host" disease.

There are times when the individual's immunological response causes more damage or discomfort than the invading microbes or foreign material, as in the case of allergic reactions. Suppression of the immune response in these cases would be desirable.

Occasionally, the immunological mechanisms become sensitized to some part of the individual's own body causing interference with or even destruction of that part. The ability to distinguish between "self" and "not self" is impaired and the body begins to destroy itself. This can result in an autoimmune diseases such as rheumatoid arthritis, insulin-dependent diabetes mellitus (which involves the autoimmune destruction of the B-cells of the islets of Langerhans which are responsible for the secretion of insulin), certain hemolytic anemias, rheumatic fever, thyroidiris, ulceractive colitis, myestheniagravis, glomerulonephritis, allergic encephalo-myelitis, continuing nerve and liver destruction which sometimes follows vital hepatitis, multiple sclerosis and systemic lupus erythematosus. Some forms of autoimmunity come about as the result of trauma to an area usually not exposed to lymphocytes such as neural tissue or the lens of the eye. When the tissues in these areas become exposed to lymphocytes, their surface proteins can act as antigens and trigger the production of antibodies and cellular immune responses which then begin to destroy those tissues. Other autoimmune diseases develop after exposure of the individual to antigens which are antigenically similar to, that is cross-react with, the individual's own tissue. Rheumatic fever is an example of this type of disease in which the antigen of the streptococcal bacterium which causes rheumatic fever is cross-reactive with parts of the human heart. The antibodies cannot differentiate between the bacterial antigens and the heart muscle antigens and cells with either of those antigens can be destroyed. Suppression of the immune system in these autoimmune diseases would be useful in minimizing or eliminating the effects of the disease. Certain of these autoimmune diseases, for example, insulin-dependent diabetes mellitus, multiple sclerosis and rheumatoid arthritis, are characterized as being the result of a cell-mediated autoimmune response and appear to be due to the action of T-cells [See Sinha et al. Science 248, 1380 1990)]. Others, such as myestheniagravis and systemic lupus erythematosus, are characterized as being the result of a humoral autoimmune response [Id.].

Suppression of the immune response would thus be useful in the treatment of patients suffering from autoimmune diseases. More particularly, suppression of cell-mediated immune response would thus be useful in the treatment of patients suffering from autoimmune diseases due to the action of T-cells such as insulin-dependent diabetes mellitus, multiple sclerosis and rheumatoid arthritis. Suppression of humoral immune response would be useful in the treatment of patients suffering from T-cell independent autoimmune diseases such as myestheniagravis and systemic lupus erythematosus.

SUMMARY OF THE INVENTION

The present invention provides a method of effecting immunosuppression in a patient in need thereof comprising administering to said patient an effective immunosuppressive amount of a compound of formula (1)

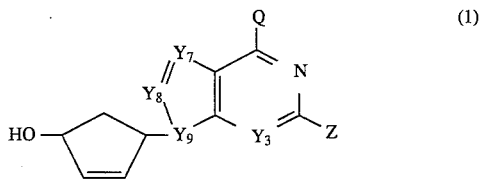

(1)

wherein
the hydroxy substituent on the cyclopentenyl ring is in the CIS configuration relative to the bicyclic substituent,
$Y_3$, $Y_7$, $Y_8$ and $Y_9$ are each independently nitrogen or a CH group,
Q is $NH_2$, halogen or hydrogen, and
Z is hydrogen, halogen, or $NH_2$;
or a pharmaceutically-acceptable salt thereof.

The present invention also provides a method of suppressing adaptive immunity in a patient in need thereof comprising administering to said patient an effective immunosuppressive amount of a compound of formula (1).

In addition, the present invention provides a pharmaceutical composition comprising an effective immunosuppressive amount of a compound of formula (1) in admixture or otherwise in association with one or more pharmaceutically acceptable carriers or excipients.

DETAILED DESCRIPTION OF THE INVENTION

As used herein the term "halogen" refers to monovalent iodine, bromine, chlorine or fluorine radicals, the term "nitrogen" refers to a trivalent nitrogen radical and the term "CH group" refers to a methylidyne radical.

As used herein, the term "pharmaceutically-acceptable salts" refers to acid addition salts of the compounds of formula (1) wherein the toxicity of the compound is not increased compared to the non-salt. Representative examples of pharmaceutically-acceptable salts, which are made by treating the compounds of formula (1) with the corresponding acids, are: hydrobromide, hydrochloride, sulfuric, phosphoric, nitric, formic, acetic, propionic, succinic, glycolic, lactic, malic, tartaric, citric ascorbic, α-ketoglutaric, glutamic, aspartic, maleic, hydroxymaleic, pyruvic, phenylacetic, benzoic, paraaminobenzoic, anthranilic, parahydroxybenzoic, salicylic, para-aminosalicylic, methanesulfonic, ethanesulfonic, hydroxyethanesulfonic, ethylenesulfonic, halobenzenesulfonic, toluenesolfonic, naphthalenesulfonic and sulfanilic acids. The hydrochloride is preferred as the pharmaceutically-acceptable salt of compounds of formula (1).

It is understood that the hydroxy substituent on the cyclopentenyl ring of the compounds of formula (1) have a CIS configuration relative to the bicyclic substituent. It is further understood that these compounds of formula (1) may exist in a variety of stereoisomeric configurations. Of course the compounds of formula (1) encompass and include both the individual stereoisomers and racemic mixtures thereof.

A general synthetic procedure for preparing compounds of formula (1) wherein $Y_9$ is nitrogen is set forth in Scheme A.

Scheme A

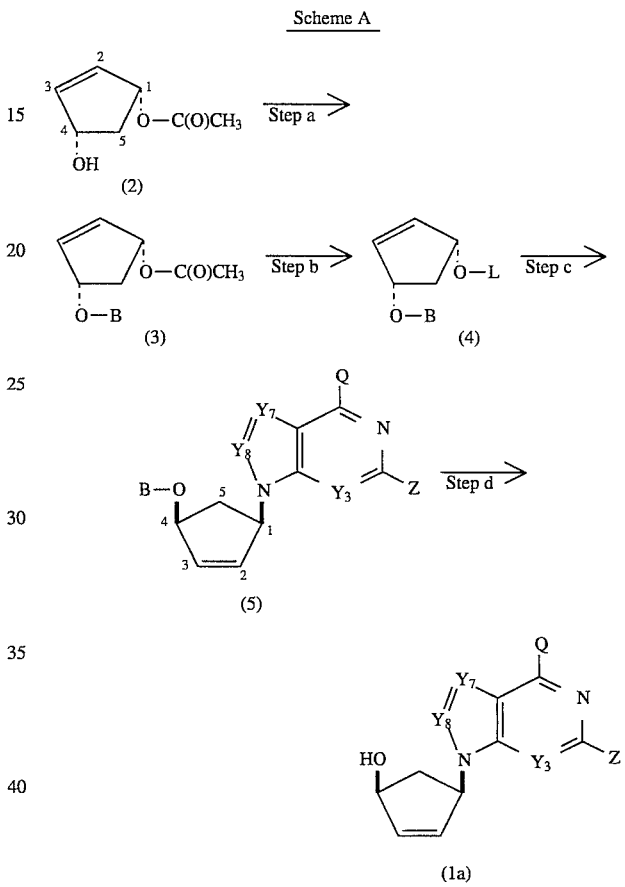

B = Blocking group; L = Leaving group

In step a, the reactive 4-hydroxy moiety of (1R, 4S)-Cis-1-acetoxy-2-cyclopenten-4-ol (2) is blocked with a hydroxy protecting group (B) to form the corresponding 4-hydroxy-blocked (1R, 4S)-Cis-1-acetoxy-2-cyclopenten-4-ol (3). The particular hydroxy protecting group used can be one of many conventional hydroxy protecting groups which are well known and appreciated in the art. The selection and utilization of particular blocking groups are well known to one of ordinary skill in the art. In general, blocking groups should be selected which adequately protect the hydroxy group during subsequent synthetic steps and which are readily removable under conditions which will not cause degradation of the desired product.

Representative examples of suitable hydroxy blocking groups are tetrahydropyranyl, methoxymethyl, t-butyldimethylsilyl, methoxyethoxy-methyl, acetoxy and the like. The preferred blocking group for the 4-hydroxy moiety of (2) is a 2-tetrahydropyranyl group. Where it is desired to block the 4-hydroxy of (2) with a 2-tetrahydropyranyl group, (2) can be reacted with 3,4-dihydro-2H-pyran in the presence of trifluoroacetic acid to yield the corresponding (1R,4S)-Cis-1-acetoxy-4-(2-tetrahydropyranyloxy)-2-cyclopentene.

In step b, the 1-acetoxy group of the 4-hydroxy-blocked (1R, 4S)-Cis-1-acetoxy-2-cyclopenten-4-ol (3) is hydrolyzed and the resulting 1-hydroxy is derivatized with a suitable leaving group (L) to form the corresponding 2-cyclopentene derivative (4). The 1-acetoxy group of (3) is first hydrolyzed with a base such as potassium hydroxide, sodium hydroxide or ammonium hydroxide in methanol or ethanol. The 1-hydroxy group of the hydrolyzed derivative thus formed is then derivatized with a leaving group (L). The particular leaving group used can be one of many conventional leaving groups which are well known and appreciated in the art. The selection and utilization of particular leaving groups are well known to one of ordinary skill in the art. In general, the leaving group should be selected which adequately facilitates a displacement of the leaving group by an appropriate nucleoside base derivative to obtain a product with retention of configuration. Representative examples of suitable leaving groups are trillate, brosyl, tosyl, methanesulfonyl and the like. The preferred leaving group for step b is a methanesulfonyl group.

For example, where it is desired to convert the 4-hydroxy-blocked (1R, 4S)-Cis-1-acetoxy-2-cyclopenten-4-ol (3) to the corresponding 4-hydroxy-blocked (1R, 4S)-Cis-1-methanesulfonyloxy-2-cyclopenten-4-ol, (3) can be hydrolyzed with KOH in ethanol and the resulting free alcohol can then be isolated and converted to the corresponding 4-hydroxy-blocked (1R, 4S)-Cis-1-methanesulfonyloxy-2-cyclopenten-4-ol by treatment with methanesulfonyl chloride in the presence of triethylamine.

In step c, the 2-cyclopentene derivative (4) bearing a leaving group in the 1-position and a blocked hydroxy group in the 4-position, is subjected to a displacement by the desired nucleoside base (wherein $Y_9$ is nitrogen) to give the corresponding 3-hydroxy blocked carbocyclic nucleoside analog (5) with retention of configuration. For example, where it is desired to convert a 4-hydroxy-blocked (1R, 4S)-Cis-1-methanesulfonyloxy-2-cyclopentene-4-ol to the corresponding 3-hydroxy-blocked (1R,3S)-Cis-1-(9-adenyl)-4-cyclopenten-3-ol, the methanesulfonyloxy derivative can be treated with adenine in the presence of sodium hydride.

In step d, the 3-hydroxy blocked carbocyclic nucleoside analog (5) is de-blocked according to standard procedures and techniques well known and appreciated in the art to give the corresponding carbocyclic nucleoside analog (1a). For example, where the 3-hydroxy is blocked with a 2-tetrahydropyranyl group, the 3-hydroxy blocking group can be removed by treatment with acid, such as hydrochloric acid.

Alternatively, compounds of formula (1) wherein $Y_9$ is nitrogen can be prepared according to the following shortened version of Scheme A. The reactive 4-hydroxy moiety of (1S,4R)-Cis-1-acetoxy-2-cyclopenten-4-ol can be derivatized with a suitable leaving group (L) as described for step b of Scheme A. The most preferred leaving group for this alternative scheme is a mesylate group. The thus formed 2-cyclopentene derivative bearing an acetoxy group in the 1-position and a leaving group such as a mesylate group in the 4-position is then subjected to a displacement by the desired nucleoside base (wherein $Y_9$ is nitrogen) to give the corresponding 3-hydroxy blocked carbocyclic nucleoside analog (5) as described for step c of Scheme A. The compounds of formula (1) wherein $Y_9$ is nitrogen are then prepared according to step d of Scheme A.

The following example presents a typical synthesis as described by Scheme A. This example is understood to be illustrative only and is not intended to limit the scope of the invention in any way. As used herein, the following terms have the indicated meanings: "g" refers to grams; "mmol" refers to millimoles; "mL" refers to milliliters; "DMF" refers to dimethylformamide; "° C." refers to degrees Celsius; "mg" refers to milligrams; "N" refers to the normality of a solution; "psi" refers to pounds per square inch.

EXAMPLE 1

(1R,3S)-Cis-1-(9-adenyl)-3-hydroxy-4-cyclopentene hydrochloride

Step a: (1R,4S)-Cis-1-acetoxy-4-(2-tetrahydropyranyloxy)-2-cyclopentene

To a stirring solution of (1R,4S)-Cis-1-acetoxy-2-cyclopenten-4-ol (1 g, 7.0 mmol) in 20 mL of dichloromethane add 3,4-dihydro-2H-pyran (0.6 g, 7.1 mmol) and 5 drops of trifluoroacetic acid. Stir the mixture for 24 hours. Dilute the mixture with 50 mL of dichloromethane and extract with saturated sodium bicarbonate and then brine. Dry the organic layer over sodium sulfate. Remove the solvent under vacuum to yield the title compound (1.58 g).

Step b: (1R,4S)-Cis-1-methanesulfonyloxy-4-(2-tetrahydropyranyloxy)-2-cyclopentene Dissolve (1R,4S)-Cis-1-acetoxy-4-(2-tetrahydropyranyloxy)-2-cyclopentene (3.0 g, 13 mmol) in 50 mL of absolute ethanol. To this solution add potassium hydroxide (0.8 g, 14 mmol) and allow the mixture to stir for 3 hours. Concentrate the mixture and apply to a silica gel column (10 g) eluting with ethyl acetate/hexane (1:1). Remove the solvent to yield (1R,4S)-Cis-4-(2-tetrahydropyranyloxy)-2-cyclopenten-1-ol as a colorless oil (2.38 g). Dissolve (1R,4S)-Cis-4-(2-tetrahydropyranyloxy)-2-cyclopenten-1-ol (1.2 g, 6.6 mmol) in 25 mL of dichloromethane and to this solution add methanesulfonyl chloride (1.13 g, 9.9 mmol) and triethylamine (0.93 g, 9.2 mmol). Stir the reaction for 45 minutes, then extract the reaction mixture with water, brine, and then dry the organic layer over sodium sulfate. Concentrate the solution to yield the title compound (1.62 g, 94% yield) as a yellow oil.

Step c: (1R,3S)-Cis-1-(9-adenyl)-3-(2-tetrahydropyranyloxy)-4-cyclopentene

Add sodium hydride (80%, 0.57 g, 19.8 mmol) to a stirring suspension of adenine (2.67 g, 19.8 mmol) in 100 mL of DMF at 60° C. After stirring for 3 hours at 60° C., add (1R,4S)-Cis-1-methanesulfonyloxy-4-(2-tetrahydropyranyloxy)-2-cyclopentene (1.62 g, 6.2 mmol) and continue stirring at 60° C. for 1 hour. Cool the reaction mixture to room temperature and stir overnight. The next day, heat the reaction mixture to 60° C. for 6 hours and then allow to cool to room temperature overnight. Remove the DMF under vacuum and take the residue up in stirring dichloromethane and water. Remove the organic layer, extract it with brine and then dry it over sodium sulfate. Remove the solvent under vacuum and dissolve the residue in dichloromethane. Apply the solution to a silica gel column (10 g) eluting with dichloromethane/ethanol (19:1) to yield the title compound (500 mg, 26.7% yield).

Step d: (1R,3S)-Cis-1-(9-adenyl)-3-hydroxy-4-cyclopentene hydrochloride

Dissolve (1R,3S)-Cis-1-(9-adenyl)-3-(2-tetrahydropyranyloxy)-4-cyclopentene (0.5 g, 1.7 mmol) in 50 mL of distilled water and 1.5 mL of 6N hydrochloric acid. Stir the mixture for 12 hours at room temperature and then concentrate to dryness under vacuum. Take the residue up in ethanol with enough ammonium hydroxide to effect a solution, and then add an equal volume of dichloromethane (ammonium chloride precipitates). Apply the mixture to a silica gel column (50 g, 70–230 mesh) eluting with dichloromethane/methanol (4:1) and recovering the title compound in 40 mL fractions. Combine and concentrate the fractions containing pure material to dryness. Dissolve the residue in ethanol and add enough 6N HCl to adjust the pH to 1. Concentrate the solution to dryness to yield the title compound (230 mg, 62% yield). $[\alpha]_{365}=+372°$ (methanol, 0.36 mg/mL). $H^1$-NMR(DMSO/TMS) δ=8.6(s,1H), 8.5(s, 1H), 6.3(m,1H), 6.0(m,1H), 5.6(m,1H), 4.8(m,1H), 3.1(q, 1H), 1.85(dt,1H).

The following compounds can be prepared by procedures analogous to those described above for Example 1 using readily available starting materials:

- (1R,3S)-Cis-1-[9-(3-deazaadenyl)]-3-hydroxy-4-cyclopentene hydrochloride
- (1R,3S)-Cis-1-[9-(7-deazaadenyl)]-3-hydroxy-4-cyclopentene hydrochloride
- (1R,3S)-Cis-1-[9-purinyl]-3-hydroxy-4-cyclopentene hydrochloride
- (1R,3S)-Cis-1-[9-(8-azaadenyl)]-3-hydroxy-4-cyclopentene hydrochloride, melting point 200° C. (decomp)
- (1R,3S)-Cis-1-[9-(2-aminopurinyl)]-3-hydroxy-4-cyclopentene hydrochloride
- (1R,3S)-Cis-1-[9-(2,6-diaminopurinyl)]-3-hydroxy-4-cyclopentene hydrochloride, melting point 160° C. (decomp, lypholized)
- (1R,3S)-Cis-1-[9-(2-amino-6-chloropurinyl)]-3-hydroxy-4-cyclopentene hydrochloride.

The starting materials for the synthetic scheme described above, including (1R, 4S)-Cis-1-acetoxy-2-cyclopenten-4-ol, adenine, 7-deazaadenine, purine, 8-azaadenine, 2-aminopurine, 2,6-diaminopurine and 2-amino-6-chloropurine, are readily available or can be made according to conventional procedures and techniques well known and appreciated in the art.

A general synthetic procedure for preparing compounds of formula (1) wherein $Y_8$ and $Y_9$ are each a CH group is set forth in Scheme B.

Scheme B

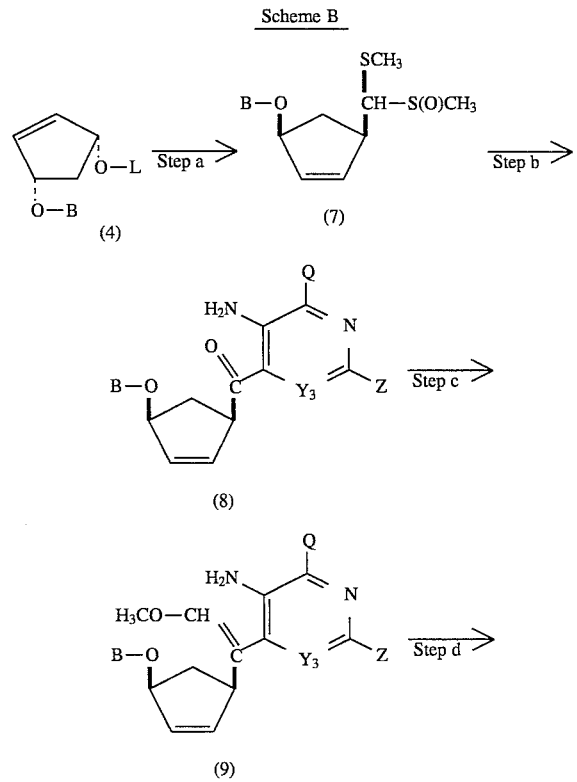

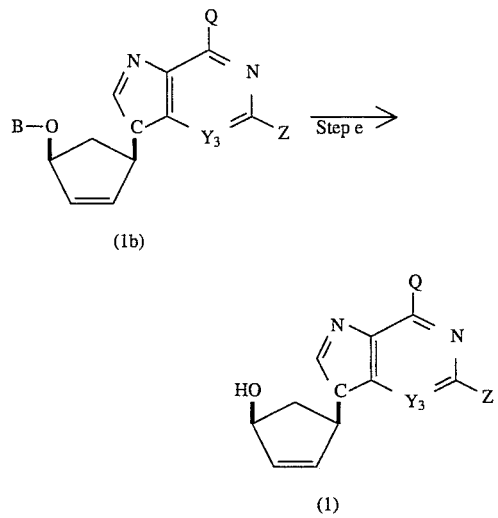

In step a, the 2-cyclopentene derivative (4) is reacted with the sodium anion of methyl methylsulfinylmethyl sulfide to yield the corresponding 1-substituted derivative (7).

In step b, the sodium anion of (7) is reacted with the appropriate pyrimidine or pyridine derivative, such as 5-amino-4,6-dichloropyrimidine, followed by hydrolysis to give the corresponding ketone derivative (8).

In step c, the ketone derivative (8) is converted to the corresponding enol ether (9) by reacting (8) with the appropriate Wittig reagent, such as $\phi_3P=CH_2OCH_3$ [methoxymethyl triphenylphosphylidine chloride], in the presence of n-butyllithium.

In step d, the enolate (9) is cyclized in the presence of acid, such as HCl, to give the 6-substituted nucleoside analog (1b).

In step e, the 3-hydroxy blocking group is removed according to standard techniques well known and appreciated in the art to give the nucleoside analog (1). Where the 6-substituted nucleoside analog (1b) bears a chlorine in the 6-position, the 6-chloro derivative can be converted to the 6-amino or 6-hydrogen derivative according to standard techniques well known and appreciated in the art.

The following example presents a typical synthesis as described by Scheme B. This example is understood to be illustrative only and is not intended to limit the scope of the invention in any way.

EXAMPLE 2

(1R,3S)-Cis-1-[9-(9-deazaadenyl)]3-hydroxy-4-cyclopentene hydrochloride

Step a: (1R,4S)-Cis-4-t-butyldimethylsilyloxy-1-[methyl(1-methylsulfinyl-1-methylsulfide)]-2-cyclopentene To a stirring solution of methyl methylsulfinylmethyl sulfide (1.2 equivalents) in THF at 0° C. add n-butyl lithium (1.2 equivalents) and allow to stir for 15 minutes. Over a 15 minute period, add dropwise a solution of (1R,4S)-Cis-1-methanesulfonyloxy-4-t-butyldimethylsilyloxy-2-cyclopentene (1 equivalent) in THF and allow to stir for several hours at 0° C. to 25° C. Dilute the reaction with water and extract with ethyl acetate or methylene chloride. Wash the organic layer with water, brine, and dry over sodium sulfate. Concentrate the solution to dryness to yield the title compound as a crude product.

11

Step b: (1R,4S)-Cis-4-t-butyldimethylsilyloxy-1-[carbonyl(4-[5-amino-6-chloropyrimidine])]-2-cyclopentene To a stirring solution of (1R,4S)-Cis-4-t-butyldimethylsilyloxy-1-[methyl(1-methylsulfinyl-1methylsulfide)]-2-cyclopentene (1 equivalent) in THF at 0° C. add n-butyllithium and continue stirring for 15 minutes. Over a 15 minute period, add dropwise a solution of 5-amino-4,6-dichloropyrimidine (1.1 equivalents) in THF and stir the reaction mixture for 24 hours at room temperature. Dilute the reaction with water and extract with ethyl acetate or methylene chloride. Wash the organic layer with water, brine, and dry over sodium sulfate. Concentrate the solution to dryness to yield the title compound as a crude product. Purify the title compound using a silica gel column eluting with ethyl acetate/hexane.

Step c: (1R,4S)-Cis-4-t-butyldimethylsilyloxy-1-[ethylene-1-(4-[5-amino-6-chloropyrimide])-2-methoxy]-2-cyclopentene To a stirring suspension of methoxymethyl triphenylphosphylidine chloride (1.2 equivalents) in THF at 0° C. add n-butyllithium (1.2 equivalents) followed by stirring for 1 hour. Over a 15 minute period, add (1R,4S)-Cis-4-t-butyldimethylsilyloxy-1-[carbonyl(4-[5-amino-6-chloropyrimidine])]-2-cyclopentene (1 equivalent) in THF and stir overnight at 0° C. Concentrate the reaction mixture to dryness and dissolve the residue in diethyl ether. Cool to 0° C. for 1 hour and remove the precipitate (lithium chloride and triphenylphosphineoxide) by filtration. Concentrate the filtrate to yield the title compound. Purify the title compound using a silica gel column eluting with ethyl acetate/hexane.

Step d: (1R,3S)-Cis-3-t-butyldimethylsilyloxy-1-[9-(6-chloro-9-deazapurinyl)]-4-cyclopentene Dissolve (1R,4S)-Cis-4-t-butyldimethylsilyloxy-1-[ethylene-1-(4-[5-amino-6-chloropyrimidine])-2-methoxy]-2-cyclopentene in aqueous methanol and a sufficient amount of 6 N HCl and stir at room temperature for 4 hours. Neutralize the product with ammonium hydroxide and concentrate the reaction mixture to dryness to yield the title compound. Purify the product using a silica gel column eluting with methylene chloride/ethanol.

Step e: (1R,3S)-Cis-1-[9-(9-deazaadenyl)]-3-hydroxy-4-cyclopentene Hydrochloride Enclose (1R,3S)-Cis-3-t-butyldimethylsilyloxy-1-[9-(6-chloro-9-deazapurinyl)]-4-cyclopentene in a sealed container of methanol and anhydrous ammonia for 24 hours applying heat if necessary. Remove the solvent and apply the product to a Dowex 50W™ column eluting with dilute ammonium hydroxide. Concentrate the eluant to dryness, take up in water, make acidic with 6 N HCl and stir for 4 hours. Concentrate the solution to dryness to yield the title compound.

A general synthetic procedure for preparing compounds of formula (1) wherein $Y_9$ is a CH group and $Y_8$ is a nitrogen is set forth in Scheme C.

Scheme C

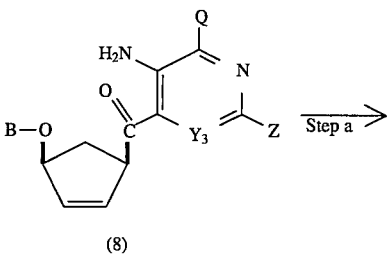

(8)

-continued
Scheme C

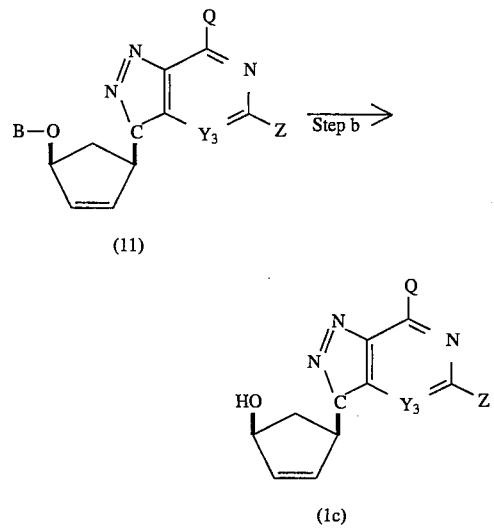

In step a, the ketone derivative (8), made as described in Scheme B, is converted to the corresponding oxime derivative and then cyclized to the corresponding 8-aza-9-deaza-6-substituted-nucleoside derivative (11) by reacting the oxime with diethylazodicarboxylate (DEAD) and triphenylphosphine.

In step b, the 3-hydroxy blocking group of (11) is removed according to standard techniques well known and appreciated in the art to give the nucleoside analog (1c). Where the nucleoside analog (1c) bears a chlorine in the 6-position, the 6-chloro derivative can be converted to the 6-amino or 6-hydrogen derivative according to standard techniques well known and appreciated in the art.

EXAMPLE 3

(1R,3S)-Cis-1-[9-(8-aza-9-deazaadenyl)]3-hydroxy-4-cyclopentene hydrochloride

Step a: (1R,3S)-Cis-3-t-butyldimethylsilyloxy-1-(9-[8-aza-6-chloro-9-deazapurinyl])-4-cyclopentene To a solution of (1R,4S)-Cis-4-t-butyldimethylsilyloxy-1-[carbonyl (4-[5-amino-6-chloropyrimidine])]-2-cyclopentene (1 equivalent) and hydroxylamine hydrochloride (1.2 equivalents) in dry methanol add a solution of sodium hydroxide (1.2 equivalents). After 2 hours add water and collect and dry the solid thus formed (oxime intermediate). Dissolve the oxime intermediate (1 equivalent) in methylene chloride followed by DEAD (1.2 equivalents) and triphenylphosphine (1.1 equivalents). Allow the mixture to react for 2 hours to yield the title compound. Extract the reaction mixture with water and then brine. Dry the organic layer over sodium sulfate, concentrate to dryness and add diethyl ether to precipitate out the triphenylphosphine oxide. Remove the precipitate by filtration and purify the product on a silica gel column eluting with ethyl acetate/hexane.

Step b: (1R,3S)-Cis-1-[9,(8-aza-9-deazaadenyl) ]-3-hydroxy-4-cyclopentene Hydrochloride Enclose (1R, 3S) -Cis-3-t-butyldimethylsilyloxy-1-(9-[8-aza-6-chloro-9-deazapurinyl])-4-cyclopentene in a sealed container of methanol and anhydrous ammonia for 24 hours applying heat if necessary. Remove the solvent and apply the product to a Dowex 50W™ column eluting with dilute ammonium hydroxide. Concentrate the eluant to dryness, take up in water, make acidic with 6 N HCl and stir for 4 hours. Concentrate the solution to dryness to yield the title compound.

In general, where it is desired to synthesize the corresponding (1S,3R) enantiomer of the compounds of formula (1), procedures similar to those described above may be followed, except that instead of blocking the 4-hydroxy group of the intermediate (2) (so that a leaving group may be attached to the 1-position after hydrolysis of the acetoxy group), an appropriate leaving group is attached at the 4-position leaving the 1-acetoxy group or other appropriate blocking group at the 1-position.

For example, a general synthetic procedure for preparing the corresponding (1S,3R) enantiomers of the compounds of formula (1) wherein $Y_9$ is nitrogen is set forth in Scheme D.

In step a, the 4-hydroxy moiety of (1R,4S)-Cis-1-acetoxy-2-cyclopenten-4-ol (2) is derivatized with a suitable leaving group (L), by procedures as described in Scheme A, to form the corresponding 2-cyclopentene derivative (4a). Representative examples of suitable leaving groups are trillate, brosyl, tosyl, methanesulfonyl and the like. The preferred leaving group is a methanesulfonyl group.

In step b, the 2-cyclopentene derivative (4a) bearing a leaving group in the 4-position and an acetoxy group in the 1-position, is subjected to a displacement by the desired Scheme D

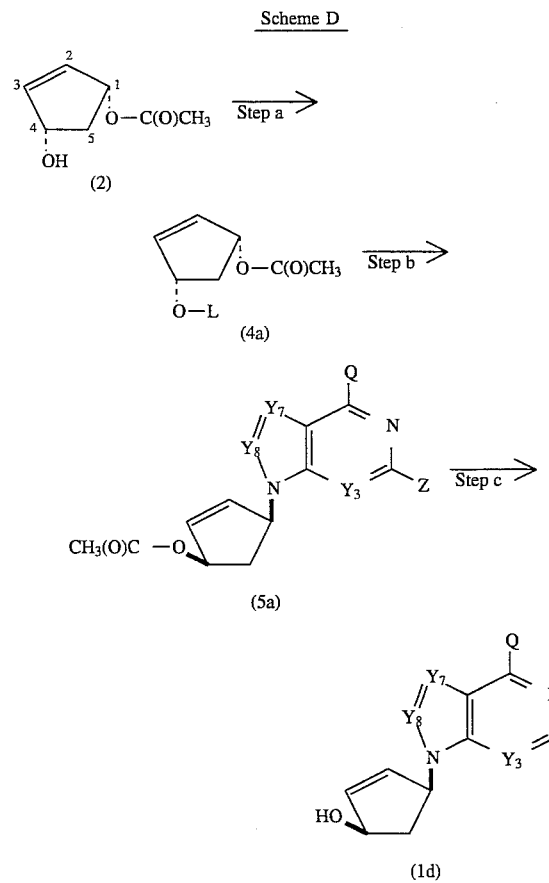

L =Leaving group nucleoside base (wherein $Y_9$ is nitrogen) to give the corresponding 1-acetoxy-carbocyclic nucleoside analog (5a) with retention of configuration. This reaction may be carried out as described for the displacement reaction in Scheme A.

In step c, the 1-acetoxy group of the 1-acetoxycarbocyclic nucleoside analog (5a) is removed according to standard procedures and techniques well known and appreciated in the art to give the corresponding carbocyclic nucleoside analog (1d)). For example, the 1-acetoxy group can be removed by treatment with base, such as potassium carbonate.

The following example presents a typical synthesis as described by Scheme D. This example is understood to be illustrative only and is not intended to limit the scope of the invention in any way.

EXAMPLE 4

(1S,3R)-Cis-1-(9-adenyl)-3-hydroxy-4-cyclopentene hydrochloride

Step a: (1S,4R)-Cis-1-methanesulfonyloxy-4-acetoxy-2-cyclopentene

Dissolve (1R,4S)-Cis-1-acetoxy-2-cyclopenten-4-ol (1.42 g, 10.0 mmol) in 40 mL of dichloromethane. To this solution, add methanesulfonyl chloride (3.72 g, 30.0 mmol) and triethylamine (3.63 g, 30.0 mmol) and allow to stir for 4.5 hours. Extract the mixture sequentially with water and then brine. Dry the organic layer over sodium sulfate. Concentrate the solution to yield the title compound as a yellow oil (2.09 g, 95% yield). which is used immediately in the next reaction.

Step b: (1S,3R)-Cis-1-(9-adenyl)-3-acetoxy-4-cyclopentene

To a stirring suspension of adenine (4.1 g, 30.0 mmol) in 50 mL of dimethylformamide at 60° C., add sodium hydride (60%, 1.0 g, 30.0 mmol). After the solution has stirred for 3 hours at 60° C., add (1S,4R)-Cis-1-methanesulfonyloxy-4-acetoxy-2-cyclopentene (2.09 g, 9.5 mmol) and continue stirring at 60° C. for 16 hours. Remove the dimethylformamide under vacuum and take the residue up in stirring dichloromethane and water. Remove the organic layer, extract with brine and dry the organic layer over sodium sulfate. Remove the solvent under vacuum and dissolve the residue in dichloromethane. Apply the solution to a silica gel column (40 g) and elute with chloroform/methanol (9:1)to yield the title compound (1.07 g) (33% yield).

Step c: (1S,3R)-Cis-1-(9-adenyl)-3-hydroxy-4-cyclopentene hydrochloride

Dissolve (1S,3R)-Cis-1-(9-adenyl)-3-acetoxy-4-cyclopentene (0.5 g, 1.7 mmol) in 25 mL of methanol, then add 3 mL water and then 600 mg $K_2CO_3$. Stir the mixture for 1 hour at room temperature, and then concentrate the mixture to dryness under vacuum. Take up the solid in ethanol to precipitate $K_2CO_3$ and filter the mixture. Add an equal amount of dichloromethane. Apply the mixture to a silica gel column (50 g, 70–230 mesh) and elute with dichloromethane/methanol (4:1). Collect fractions (40 mL) and concentrate the fractions containing pure material to dryness. Redissolve the solid in ethanol and add enough 6N HCl to adjust the pH to 1. Concentrate the solution to dryness to yield the title compound (298 mg) (62% yield).

$[\alpha]_{365}=-371°$ (MeOH, 0.76 mg/mL)

$H^1$-NMR(DMSO/TMS) δ'8.6(s,1H), 8.5(s,1H), 6.3(m, 1H), 6.0(m,1H), 5.6(m,1H), 4.8(m,1H), 3.1(q,1H), 1.85(dt,1H).

The present invention provides a method of effecting immunosuppression, and more specifically, a method of suppressing adaptive immunity, in a patient in need thereof comprising administering to said patient an effective immunosuppressive amount of a compound of formula (1).

As used herein, the term "patient" refers to a warm-blooded animal such as a mammal which is suffering from a disease, such as an autoimmune disease or "graft versus host" disease, or is in danger of rejection of a transplanted allogeneic tissue or organ. It is understood that humans, mice and rats are included within the scope of the term "patient".

Administration of a compound of formula (1) to a patient results in an immunosuppressive effect in the patient. More specifically, administration of a compound of formula (1) to a patient results in suppression of adaptive immunity in the patient. In other words, by treatment of a patient with a compound of formula (1), the adaptive immune response of the patient is inhibited or suppressed over that present in the absence of treatment.

A patient is in need of treatment with an immunosuppressive agent, such as a compound of formula (1), where the patient is suffering from an autoimmune disease, "graft versus host" disease or in order to prevent rejection of transplanted allogeneic tissues or organs. The term "autoimmune disease" refers to those disease states and conditions wherein the immune response of the patient is directed against the patient's own constituents resulting in an undesirable and often terribly debilitating condition.

Patients suffering from autoimmune diseases such as rheumatoid arthritis, endotoxic shock, insulin-dependent diabetes mellitus, certain hemolytic anemias, rheumatic fever, thyroidiris, ulceractive colitis, myestheniagravis, glomerulonephritis, allergic encephalo-myelitis, continuing nerve and liver destruction which sometimes follows viral hepatitis, multiple sclerosis and systemic lupus erythematosus are in need of treatment with an immunosuppressive agent such as a compound of formula (1). Rheumatoid arthritis, insulin-dependent diabetes mellitus and multiple sclerosis are characterized as being the result of a cell-mediated autoimmune response and appear to be due to the action of T-cells. Myestheniagravis and systemic lupus erythematosus are characterized as being the result of a humoral autoimmune response. As such, treatment of patients suffering from these diseases by administration of a compound of formula (1) will be particularly effective in preventing further deterioration or worsening of the patient's condition. Treatment of a patient at an early stage of an autoimmune disease, such as rheumatoid arthritis, insulin-dependent diabetes mellitus, multiple sclerosis, myestheniagravis or systemic lupus erythematosus, would be particularly effective in preventing further deterioration of the disease state into a more serious condition. For example, insulin-dependent diabetes mellitus (IDDM) is an autoimmune disease which is believed to result from the autoimmune response directed against the B-cells of the islets of Langerhans which secrete insulin. Treatment of a patient suffering from an early stage of IDDM prior to the complete destruction of the β-cells of the islets of Langerhans would be particularly useful in preventing further progression of the disease since it would prevent or inhibit further destruction of remaining insulin-secreting β-cells. It is understood that treatment of a patient suffering from an early stage of other autoimmune diseases will also be particularly useful to prevent or inhibit further natural progression of the disease state to more serious stages.

Patients who have received or who are about to receive an allogeneic tissue or organ transplant, such as an allogeneic kidney, liver, heart, skin, bone marrow, are also patients who are in need of prophylactic treatment with an immunosuppressive agent such as a compound of formula (1). An immunosuppressive agent will prevent the adaptive immune response of the doner from rejecting the allogeneic tissue or organ of the donor. Likewise, patients suffering from "graft versus host" disease are patients who are in need of treatment with an immunosuppressive agent such as a compound of formula (1). An immunosuppressive agent will prevent the adaptive immune response of the transplanted tissue or organ from rejecting the allogeneic tissue or organ of the doner.

Based on standard clinical and laboratory tests and procedures, an attending diagnostician, as a person skilled in the art, can readily identify those patients who are in need of treatment with an immunosuppressive agent such as a compound of formula (1).

An effective immunosuppressive amount of a compound of formula (1) is that amount which is effective, upon single or multiple dose administration to a patient, in providing an immunosuppressive effect or, more particularly, a suppression of adaptive immune response. An immunosuppressive effect refers to the slowing, interrupting, inhibiting or preventing the further expression of the adaptive immune response.

An effective immunosuppressive amount of a compound of formula (1) can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the use of concomitant medication; and other relevant circumstances.

An effective immunosuppressive amount of a compound of formula (1) is expected to vary from about 0.1 milligram per kilogram of body weight per day (mg/kg/day) to about 500 mg/kg/day. Preferred amounts are expected to vary from about 1 to about 50 mg/kg/day.

In effecting treatment of a patient, a compound of formula (1) can be administered in any form or mode which makes the compound bioavailable in effective amounts, including oral and parenteral routes. For example, compounds of formula (1) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected the disease state to be treated, the stage of the disease, and other relevant circumstances.

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable acid addition salts for purposes of stability, convenience of crystallization, increased solubility and the like.

In another embodiment, the present invention provides compositions comprising a compound of formula (1) in admixture or otherwise in association with one or more inert carriers. These compositions are useful, for example, as assay standards, as convenient means of making bulk shipments, or as pharmaceutical compositions. An assayable amount of a compound of formula (1) is an amount which is readily measurable by standard assay procedures and techniques as are well known and appreciated by those skilled in the art. Assayable amounts of a compound of formula (1) will generally vary from about 0.001% to about 75% of the composition by weight. Inert carriers can be any material which does not degrade or otherwise covalently react with a compound of formula (1). Examples of suitable inert carriers are water; aqueous buffers, such as those which are generally useful in High Performance Liquid Chromatography (HPLC) analysis; organic solvents, such as acetonitrile, ethyl acetate, hexane and the like; and pharmaceutically acceptable carriers or excipients.

More particularly, the present invention provides pharmaceutical compositions comprising an effective immunosuppressive amount of a compound of formula (1) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral or parenteral use, including topical use, and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, including topical administration, the compounds of the present invention may be incorporated into a solution or suspension. These preparations should contain at least 0.1% of a compound of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The solutions or suspensions may also include the one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

As with any group of structurally related compounds which possesses a particular generic utility, certain groups and configurations are preferred for compounds of formula (1) in their end-use application. Compounds of the formula (1) wherein $T_3$ is nitrogen are generally preferred. Compounds of the formula (1) wherein $T_7$ is nitrogen are generally preferred. Compounds of the formula (1) wherein $Y_8$ is a CH group are generally preferred. Compounds of the formula (1) wherein $Y_9$ is nitrogen are generally preferred. Furthermore, compounds of the formula (1) wherein Q is $NH_2$ and Z is hydrogen are generally preferred.

The following specific compounds of formula (1) are especially preferred:

(1R,3S)-Cis-1-(9-adenyl)-3-hydroxy-4-cyclopentene hydrochloride (1S,3R)-Cis-1-(9-adenyl)-3-hydroxy-4-cyclopentene hydrochloride (1R,3S)-Cis-1-[9-(8-azaadenyl)]-3-hydroxy-4-cyclopentene hydrochloride (1R,3S)-Cis-1-[9-(2,6-diaminopurinyl)]-3-hydroxy-4-cyclopentene hydrochloride.

The following studies illustrate the utility of the compounds of formula (1). These studies are understood to be illustrative only and are not intended to limit the scope of the invention in any way. As used herein the following terms have the indicated meanings: "µM" refers to micromolar concentration; "Units" refers to the internationally accepted measurement of protein; "S. D." refers to standard deviation; "ηmol" refers to nanomoles; "ηg" refers to nanograms.

Rat peritoneal macrophages were isolated and grown in cell culture essentially as described by Edwards et al. [Science 239,769 (1988)]. Macrophages were incubated along with opsonized zymosan (3 mg/mL), which acts as a particulate stimulus, and recombinant rat γ-interferon (rrIFN-γ)(1000Units/mL), which acts as an activating lymphokine, in the presence of various concentrations of (1R, 3S)-Cis-1(9-adenyl)-3-hydroxy-4-cyclopentene (0 to 1000 µM). The degree of macrophage priming was measured using the Superoxide Anion ($O_2^-$) assay as described by Edwards et al. [Science 239,769 (1988)]. The results of this study show that (1R,3S)-Cis-1(9-adenyl)-3-hydroxy-4-cyclopentene effectively inhibits the priming of rat macrophages inuitro with an $IC_{50}$ of 25.0 µM.

The rat air pouch model of inflammation was used to obtain rat PMNs using 25 ηg/pouch of recombinant human interleukin-1 (rHuIL-1) to elicit the cells essentially according to the method of Esser et al. [Internat. J. Tissue Reactions XI, 291 (1989)]. PMNs were incubated along with phorbol myristate acetate (PMA) (200 ηg/mL), which acts as a soluble stimulus, and rrIFN-γ(1000 Units/mL), which act as a stimulatory lymphokine, in the presence of various concentrations of (1R,3S)-Cis-1(9-adenyl)-3-hydroxy-4-cyclopentene (0 to 1000 μM). The degree of macrophage priming was measured using the Superoxide Anion ($O_2-$) assay as described by Edwards et al. [Science 239,769 (1988)]. The results of this study show that (1R,3S)-Cis-1(9-adenyl)-3-hydroxy-4-cyclopentene effectively inhibits the rrIFN-γ priming of rat PMN in vitro with an $IC_{50}$ of 0.015 μM.

What is claimed is:

1. A method of effecting immunosuppression in a patient at risk of suffering from allograft rejection comprising administering to said patient an effective immunosuppressive amount of a compound of the formula

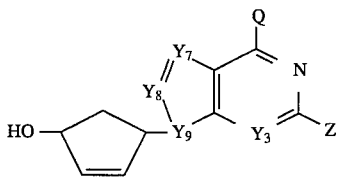

wherein the hydroxy substituent on the cyclopentenyl ring is in the CIS configuration relative to the bicyclic substituent, $Y_3$, $Y_7$, $Y_8$ and $Y_9$ are each independently nitrogen or a CH group, Q is $NH_2$, halogen or hydrogen, and Z is hydrogen, halogen, or $NH_2$;

or a pharmaceutically-acceptable salt thereof.

2. The method according to claim 1, wherein $T_3$ is nitrogen.

3. The method according to claim 1, wherein $T_7$ is nitrogen.

4. The method according to claim 1, wherein $Y_8$ is CH.

5. The method according to claim 1, wherein $Y_9$ is nitrogen.

6. The method according to claim 1, wherein Q is $NH_2$ and Z is hydrogen.

7. The method according to claim 1, wherein the pharmaceutically-acceptable salt is hydrobromide, hydrochloride, sulfuric, phosphoric, nitric, formic, acetic, propionic, succinic, glycolic, lactic, malic, tartaric, citric, ascorbic, α-ketoglutaric, glutamic, aspattic, maleic, hydroxymaleic, pyruvic, phenylacetic, benzoic, para-aminobenzoic, anthranilic, para-hydroxybenzoic, salicylic, para-aminosalicylic, methanesulfonic, ethanesulfonic, hydroxyethanesulfonic, ethylenesulfonic, halobenzenesulfonic, toluenesulfonic, naphthalenesulfonic and sulfanilic acids.

8. The method according to claim 7, wherein the pharmaceutically-acceptable salt is hydrochloride.

9. The method according to claim 1, wherein the patient is about to receive an allograft transplant.

10. The method according to claim 9, wherein the allograft transplant is an allogenic kidney, liver, heart, skin or bone marrow.

11. The method according to claim 1, wherein the patient has received an allograft transplant.

12. The method according to claim 11, wherein the allograft transplant is an allogenic kidney, liver, heart, skin or bone marrow.

* * * * *

UNITED STATES PATENT AND TRADEMARK OFFICE
CERTIFICATE OF CORRECTION

PATENT NO. : 5,605,903
DATED : February 25, 1997
INVENTOR(S) : David R. Borcherding et al It is certified that error appears in the above-indentified patent and that said Letters Patent is hereby corrected as shown below:

Column 4, Line 36 Patent reads "thyroidiris" and should read --thyroiditis--.

Column 4, Line 31 Patent reads "an autoimmune diseases" and should read --autoimmune diseases--.

Column 4, Line 39 Patent reads "vital" and should read --viral--.

Column 5, Line 57 Patent reads "hydrobromide" and should read --hydrobromic--.

Column 5, Line 57 Patent reads "hydrochloride" and should read --hydrochloric--.

Column 5, Line 64 Patent reads "toluenesolfonic" and should read --toluenesulfonic--.

Column 6, Lines 60-61 Patent reads "t-butyldim-ethylsilyl," and should read -- t-butyl-dimethylsilyl,--.

Column 7, Line 18 Patent reads "trillate" and should read --triflate--.

Column 11, Line 4 Patent reads "-1methylsulfide)]" and should read -- -1-methylsulfide--.

Column 12, Line 61 Patent reads "[9,(8-aza-9-deazaadenyl)" and should read --[9-(8-aza-9-deazaadenyl)--.

Column 13, Line 21 Patent reads "trillate" and should read --triflate--.

Column 14, Line 3 Patent reads "1$d$))." and should read --(1d).--.

Column 14, Line 26 Patent reads "yield). which" and should read --yield) which--.

Column 14, Line 60 Patent reads "8' 8.6" and should read --8=8.6--.

Column 15, Line 51 Patent reads "B-cells" and should read --β-cells--.

Column 15, Line 28 Patent reads "thyroidiris" and should read --thyroiditis--.

Column 16, Line 1 Patent reads "doner" and should read --donee--.

Column 16, Line 9 Patent reads "doner" and should read --donee--.

Column 18, Line 28 Patent reads "$T_3$" and should read --$Y_3$--.

Column 18, Line 29 Patent reads "$T_7$" and should read --$Y_7$--.

Column 18, Line 61 Patent reads "Cis-1(9-" and should read --Cis-1-(9- --.

Column 18, Line 65 Patent reads "Cis-1(9-" and should read --Cis-1-(9- --.

UNITED STATES PATENT AND TRADEMARK OFFICE
CERTIFICATE OF CORRECTION

PATENT NO. : 5,605,903
DATED : February 25, 1997
INVENTOR(S) : David R. Borcherding et al Page 2 of 2

It is certified that error appears in the above-indentified patent and that said Letters Patent is hereby corrected as shown below:

Column 18, Line 67 Patent reads "in uitro" and should read --in vitro--.

Column 19, Line 9 Patent reads "Cis-1(9-" and should read --Cis-1-(9- --.

Column 19, Line 14 Patent reads "Cis-1(9-" and should read --Cis-1-(9- --.

Column 20, Line 3 Patent reads "T$_3$" and should read --Y$_3$--.

Column 20, Line 5 Patent reads "T$_7$" and should read --Y$_7$--.

Column 20, Line 13 Patent reads "hydrobromide" and should read --hydrobromic--.

Column 20, Line 13 Patent reads "hydrochloride" and should read --hydrochloric--.

Column 20, Line 16 Patent reads "aspattic" and should read --aspartic--.

Signed and Sealed this

Fourteenth Day of July, 1998

Attest:

Attesting Officer

BRUCE LEHMAN

Commissioner of Patents and Trademarks